(12) United States Patent
Hirai et al.

(10) Patent No.: US 8,128,646 B2
(45) Date of Patent: Mar. 6, 2012

(54) ULTRASONIC VIBRATION APPARATUS

(75) Inventors: Yuji Hirai, Hachioji (JP); Masashi Yamada, Sagamihara (JP); Machiko Koshigoe, Hino (JP)

(73) Assignee: Olympus Medical Systems, Corp. (JP)

( * ) Notice: Subject to any disclaimer, the term of this patent is extended or adjusted under 35 U.S.C. 154(b) by 639 days.

(21) Appl. No.: 12/132,041

(22) Filed: Jun. 3, 2008

(65) Prior Publication Data

US 2009/0299395 A1    Dec. 3, 2009

(51) Int. Cl.
*A61B 17/32* (2006.01)
(52) U.S. Cl. .................... 606/169; 310/323.12; 310/325
(58) Field of Classification Search .................. 601/2–3; 600/471; 606/169, 39, 167, 190, 205; 310/323.12, 310/325, 326, 327, 354
See application file for complete search history.

(56) References Cited

U.S. PATENT DOCUMENTS

| | | | |
|---|---|---|---|
| 4,867,141 A | 9/1989 | Nakada et al. | |
| 5,944,737 A * | 8/1999 | Tsonton et al. | 606/205 |
| 5,989,275 A | 11/1999 | Estabrook et al. | |
| 6,278,218 B1 | 8/2001 | Madan et al. | |
| 6,569,178 B1 | 5/2003 | Miyawaki et al. | |
| 7,494,468 B2 * | 2/2009 | Rabiner et al. | 600/459 |
| 2003/0051323 A1 * | 3/2003 | Gururaja | 29/25.35 |
| 2003/0191390 A1 * | 10/2003 | Murakami | 600/439 |
| 2003/0225332 A1 * | 12/2003 | Okada et al. | 600/439 |
| 2009/0030311 A1 * | 1/2009 | Stulen et al. | 600/439 |

FOREIGN PATENT DOCUMENTS

| | | |
|---|---|---|
| DE | 37 20 424 A1 | 12/1987 |
| JP | 04-156983 | 5/1992 |
| JP | 2003-199195 | 7/2003 |

OTHER PUBLICATIONS

European Search Report dated Oct. 9, 2009 in corresponding European Patent Application No. EP 09 00 0970 (English language).
Letter from German associate dated Oct. 22, 2009 forwarding the European Search Report dated Oct. 9, 2009 to Japanese associate, including discussion of relevancy thereof. German associate's letter dated Oct. 22, 2009 was date stamped received by Japanese associate on Oct. 23, 2009 (English language).

* cited by examiner

*Primary Examiner* — Ryan Severson
*Assistant Examiner* — Rachel S Papeika
(74) *Attorney, Agent, or Firm* — Ostrolenk Faber LLP

(57) ABSTRACT

An ultrasonic vibration apparatus includes a vibrator, wherein the vibrator includes at least two vibration elements to generate ultrasonic vibration when a driving voltage is applied to the vibration elements, at least three electrode portions wherein the vibration elements and the electrode portions is alternately arranged side by side in a vibrating direction, at least the three electrode portions includes at least two first electrode portions and at least one second electrode portion alternately arranged in the vibrating direction, the vibrator integrally vibrates ultrasonically in the vibrating direction when the driving voltage is applied to the first electrode portions and the second electrode portion, and a bridging portion coupling and electrically connecting two first electrode portions of at least the two first electrode portions with each other, and the ultrasonic vibration apparatus further includes an anti-vibration portion to suppress vibration of the bridging portion in any other direction except the vibrating direction.

7 Claims, 6 Drawing Sheets

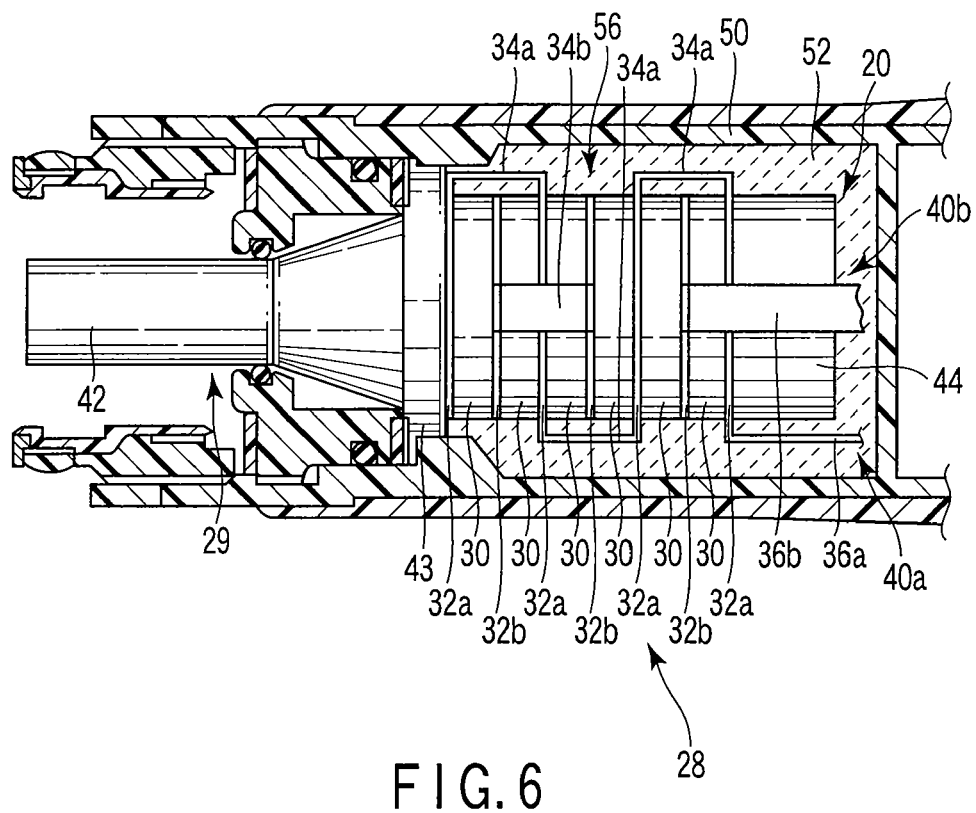
F I G. 6
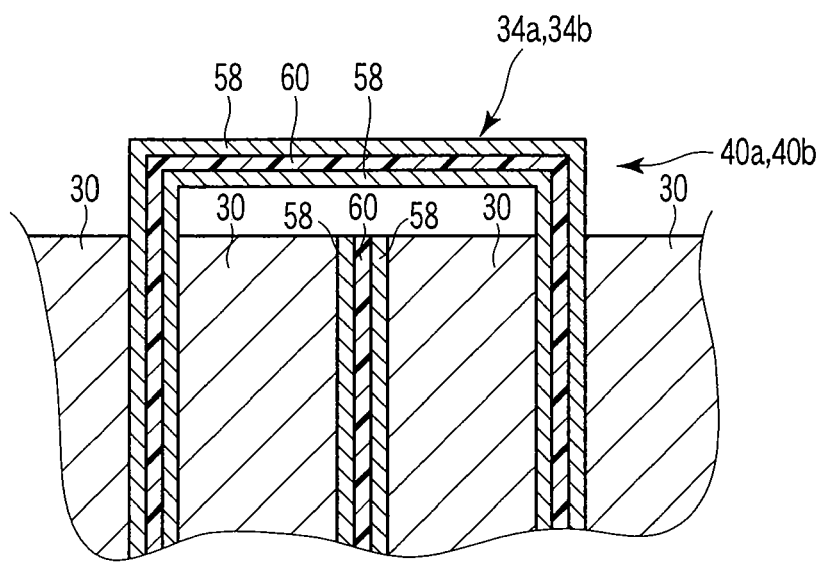
F I G. 7

ULTRASONIC VIBRATION APPARATUS

BACKGROUND OF THE INVENTION

1. Field of the Invention

The present invention relates to an ultrasonic vibration apparatus including a vibrator, the vibrator includes vibration elements and electrode portions alternately arranged side by side in a vibration direction, and the electrode portions having the same pole are sequentially coupled and electrically connected with each other by a bridging portion.

2. Description of the Related Art

Each of Jpn. Pat. Appln. KOKAI Publication No. 4-156983, a specification of U.S. Pat. No. 6,278,218, and a specification of U.S. Pat. No. 5,989,275 discloses a bolted Langevin type vibrator. In the bolted Langevin type vibrator, piezoelectric elements and electrode plates are alternately arranged side by side in a longitudinal direction. The electrode plate includes negative electrode plates and positive electrode plates alternately arranged in the longitudinal direction. The electrode plates having the same pole are sequentially coupled and electrically connected with each other by bridging portions. When driving voltage is applied to the negative electrode plates and the positive electrode plates, the driving voltage is applied to the piezoelectric elements to generate ultrasonic vibration and so the entire vibrator vibrates ultrasonically in the longitudinal direction.

BRIEF SUMMARY OF THE INVENTION

In an aspect of the present invention, an ultrasonic vibration apparatus includes a vibrator, wherein the vibrator includes: at least two vibration elements to generate ultrasonic vibration when a driving voltage is applied to the vibration elements; at least three electrode portions wherein the vibration elements and the electrode portions is alternately arranged side by side in a vibrating direction, at least the three electrode portions includes at least two first electrode portions and at least one second electrode portion alternately arranged in the vibrating direction, the vibrator integrally vibrates ultrasonically in the vibrating direction when the driving voltage is applied to the first electrode portions and the second electrode portion; and a bridging portion coupling and electrically connecting two first electrode portions of at least the two first electrode portions with each other, and the ultrasonic vibration apparatus further includes an anti-vibration portion to suppress vibration of the bridging portion in any other direction except the vibrating direction.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a partial cross-sectional side view showing a vibrator according to a fourth embodiment of the present invention;

FIG. 7 is a cross-sectional view showing a vibration generating portion according to a fifth embodiment of the present invention;

DETAILED DESCRIPTION OF THE INVENTION

Each embodiment according to the present invention will now be explained hereinafter with reference to the drawings.

Figure 1:
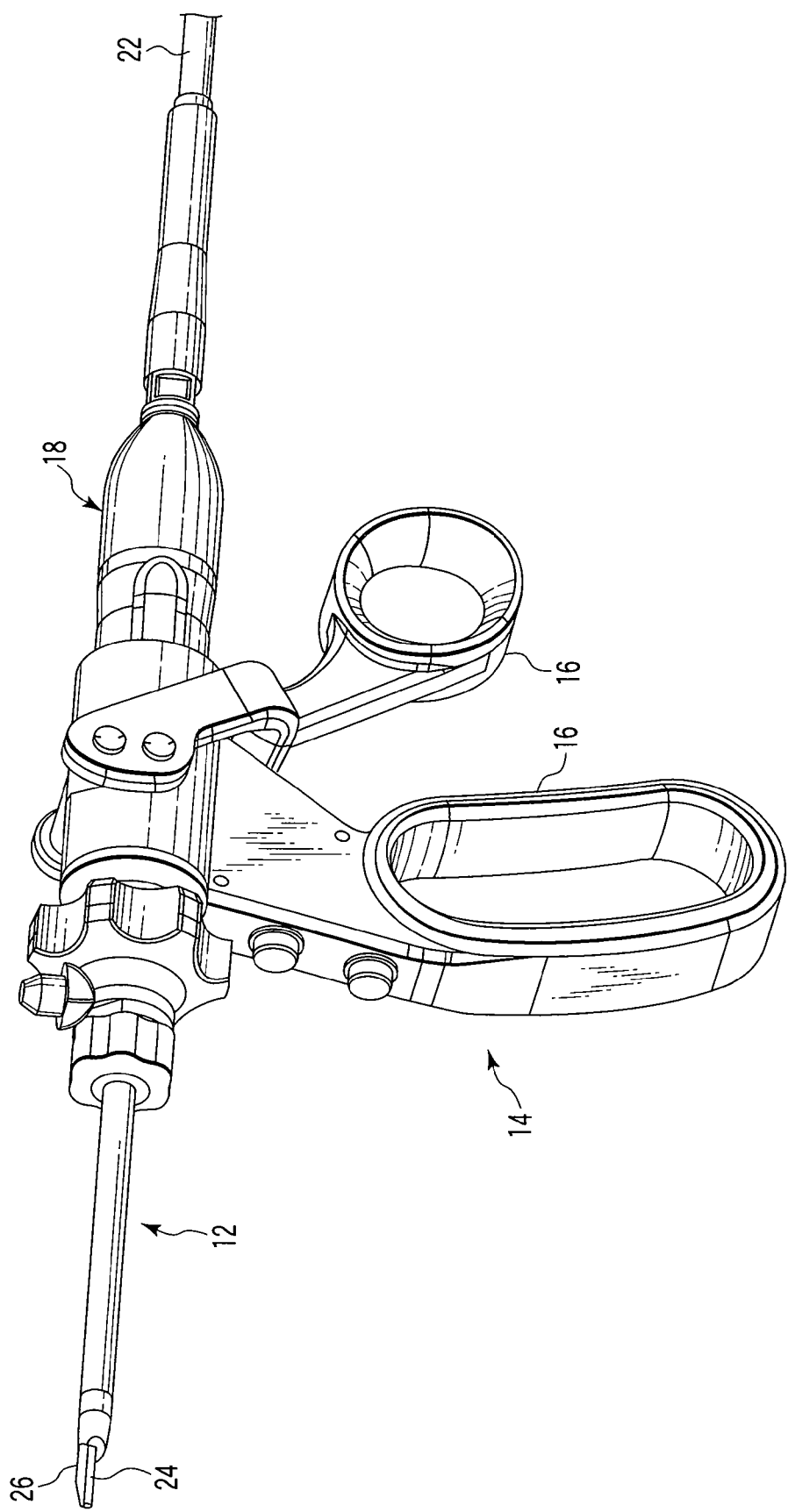
FIG. 1 is a perspective view showing an ultrasonic accessory according to a first embodiment of the present invention.
Figure 2:
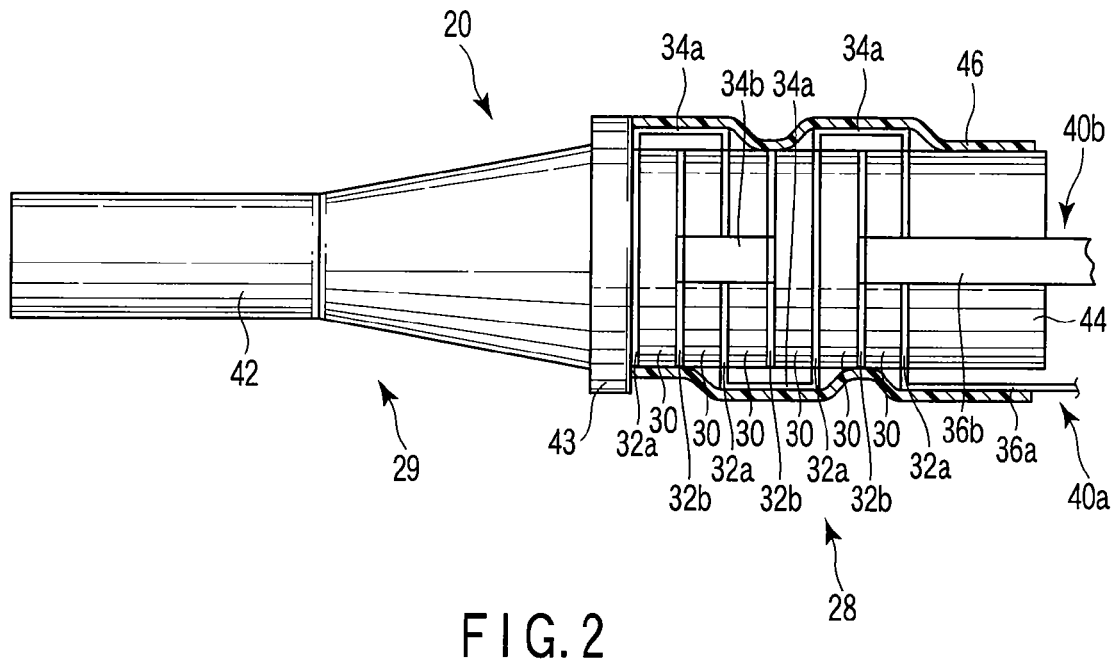
FIG. 2 is a partial cross-sectional side view showing a vibrator according to the first embodiment of the present invention.
Figure 3:
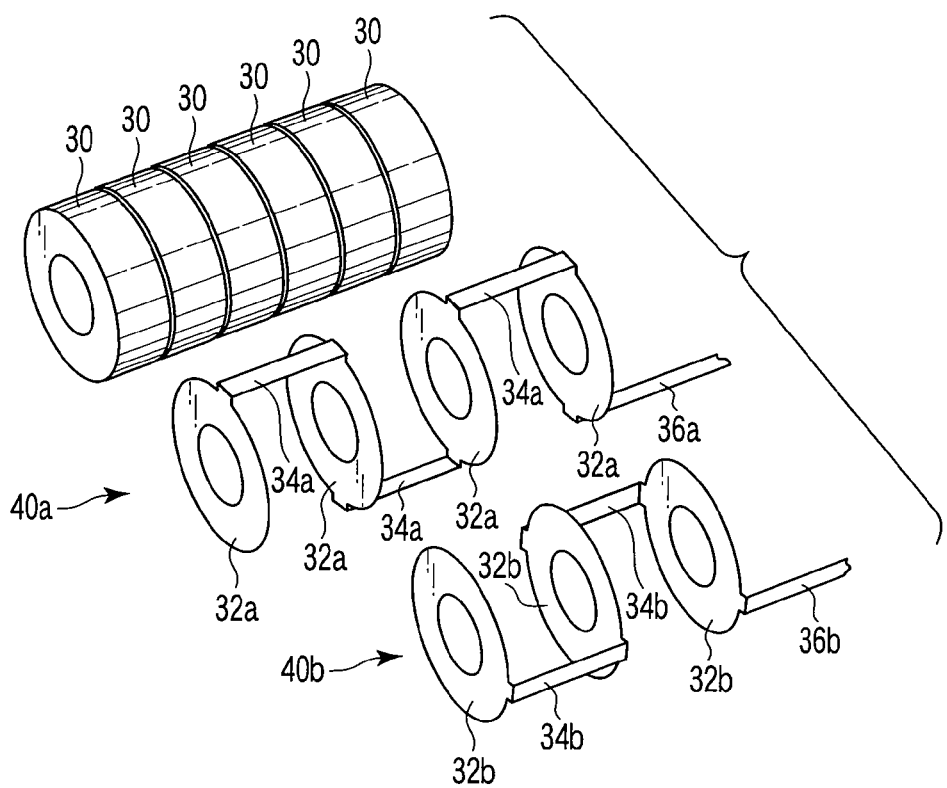
FIG. 3 is an exploded perspective view showing a vibration generating portion according to the first embodiment of the present invention.

FIGS. 1 to 3 show a first embodiment of the present invention.

An outline structure of an ultrasonic accessory will now be explained with reference to FIG. 1.

The ultrasonic accessory includes an elongated sheath unit 12. A handle unit 14 to be held and operated by an operator is coupled with a proximal end side of the sheath unit 12. A pair of handles 16 openable and closable is arranged in the handle unit 14. A vibrator unit 18 is coupled with a proximal end side of the handle unit 14. A vibrator to generate ultrasonic vibration is housed in the vibrator unit 18. An electric cord 22 is extended from the vibrator unit 18 and connected with a main body. A driving voltage is supplied to the vibrator from the main body through the electric cord 22 and so ultrasonic vibration is generated in the vibrator. A proximal end portion of an elongated probe 24 to transmit the ultrasonic vibration is coupled with a distal end portion of the vibrator. The probe 24 is inserted through the handle unit 14 and the sheath unit 12 and protruded from a distal end portion of the sheath unit 12. Further, a jaw 26 is arranged at the distal end portion of the sheath unit 12. When the pair of handles 16 in the handle unit 14 is opened or closed, the jaw 26 is opened or closed with respect to a distal end portion of the probe 24. When the distal end portion of the probe 24 and the jaw 26 grasp a living tissue and the probe 24 is vibrated ultrasonically, the living tissue is treated.

The vibrator 20 will now be explained in detail with reference to FIGS. 2 and 3.

A vibration generating portion 28 to generate the ultrasonic vibration is formed on a proximal end side of the vibrator 20. In the vibration generating portion 28, piezoelectric elements 30 each having a thick disk shape as vibration elements and electrode plates 32a and 32b each having a thin disk shape as electrode portions are coaxially alternately arranged side by side in a longitudinal direction forming a longitudinal direction of the ultrasonic accessory. As the electrode plates 32a and 32b, negative electrode plates 32a and positive electrode plates 32b are alternately arranged in the longitudinal direction. The electrode plates 32a and 32b having the same pole and adjacent to each other are coupled and electrically connected with each other by a bridging portion 34a or 34b. That is, the electrode plates 32a and 32b are sequentially coupled with each other in the longitudinal direction by the bridging portions 34a and 34b. Each of the bridging portions 34a and 34b is formed of extended portions on both ends outwardly extended in a radial direction from both the electrode plates 32a and 32b and an intermediate coupling portion extended in the longitudinal direction to couple both the extended portions. The bridging portions 34a and 34b having the same pole are arranged in the longitudinal direction to be sequentially shifted 180° along a circumferential direction, and the negative and positive bridging portions 34a and 34b are arranged in the longitudinal direction to be sequentially shifted 90° along the circumferential direction. Lead portions 36a and 36b are extended from the negative electrode plate 32a and the positive electrode plate 32b on the most proximal end, respectively, and the electrode plates 32a and 32b are electrically connected with the lead portions 36a and 36b, respectively. A voltage cable is connected with each of the lead portions 36a and 36b and led to the electric cord 22. In this embodiment, the electrode plates 32a and 32b, the bridging portions 34a and 34b, and the lead portions 36a and 36b having the same pole are formed of integral electrode members 40a and 40b processed through bending processing. A horn 42 is arranged on a distal end side of the vibration generating portion 28. The horn 42 forms a vibration transmitting portion 29 to amplify and transmit the ultrasonic vibration, has a substantially columnar shape, and is extended in the longitudinal direction. A flange portion 43 is formed at a proximal end portion of the horn 42, and a bolt is protruded from a proximal end face of the flange portion 43 toward the proximal end side. The bolt is inserted through central openings of the electrode plates 32a and 32b and the piezoelectric elements 30, and a backboard 44 is screwed into a terminal end portion of the bolt. The backboard 44 is screwed into the bolt and so the piezoelectric elements 30 and the electrode plates 32a and 32b are held between the proximal end face of the horn 42 and a distal end face of the backboard 44.

A tubular fitted-outside member 46 as an anti-vibration member is fitted on outside of the vibration generating portion 28 of the vibrator 20. The fitted-outside member 46 has insulation properties and relatively small elastic properties and is tend to contract inwardly in the radial direction. Furthermore, the fitted-outside member 46 covers the bridging portions 34a and 34b and gives the bridging portions 34a and 34b a radially inward load. In this embodiment, a heat-shrinkable tube is used as the fitted-outside member 46.

When vibrating the vibrator 20 ultrasonically, a driving voltage is applied to the negative and positive electrode member 40a and 40b through the negative and positive voltage cables. The driving voltage is applied to the respective piezoelectric elements 30 between the negative electrode plates 32a and the positive electrode plates 32b, the ultrasonic vibration is generated in the respective piezoelectric elements 30, and the entire vibrator 20 vibrates ultrasonically in the longitudinal direction. Therefore, the bridging portions 34a and 34b also vibrates ultrasonically in the longitudinal direction. Here, since the fitted-outside member 46 gives the bridging portions 34a and 34b the radially inward load and the fitted-outside member 46 prevents the bridging portions 34a and 34b from vibrating in any other direction except the longitudinal direction, occurrence of the vibration in any other direction except the longitudinal direction in the bridging portions 34a and 34b is suppressed. As a result, fatigue of the bridging portions 34a and 34b is reduced, and so fracture of the bridging portions 34a and 34b is prevented.

It is to be noted that, in the vibrator 20 in this embodiment, the horn 42 and the backboard 44 are electrically connected with each other through the bolt inserted through the central openings of the piezoelectric elements 30 and the electrode plates 32a and 32b. That is, the negative electrode plate 32a at the most proximal end, the backboard 44, the bolt, and the horn 42 are electrically connected with each other. Therefore, in a case where the flange portion 43 at the proximal end portion of the horn 42 functions as the negative electrode plate as the electrode portion, the negative electrode plate 32a adjacent to the flange portion 43 and the bridging portion 34a coupling the former negative electrode plate 32a with the negative electrode plate 32a adjacent to the former negative electrode plate 32a can be eliminated.

Figure 4:
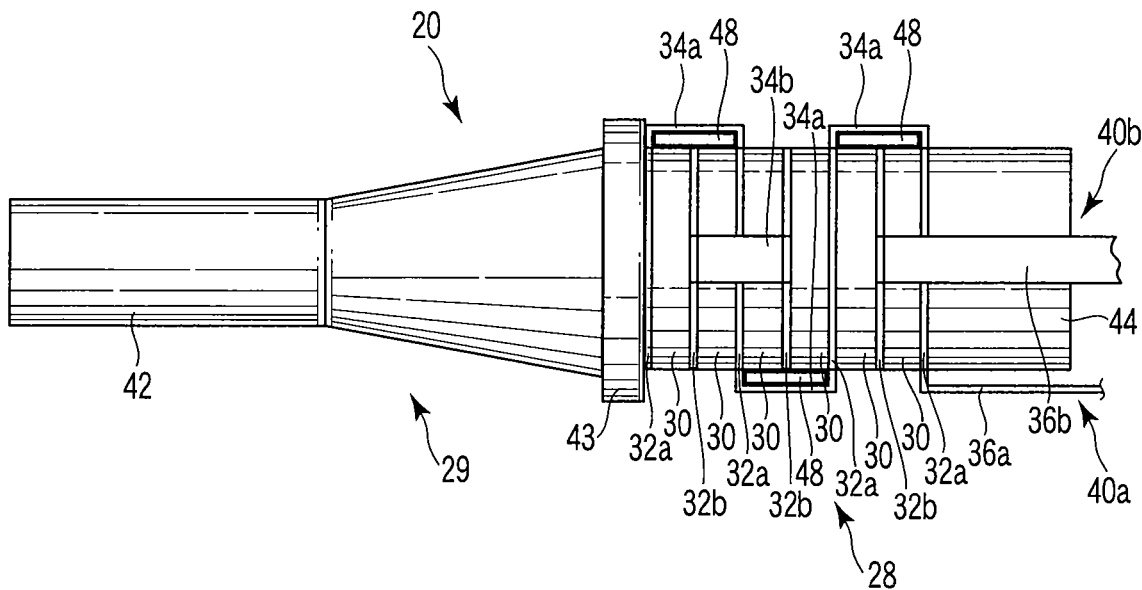
FIG. 4 is a side view showing a vibrator according to a second embodiment of the present invention.

FIG. 4 shows a second embodiment of the present invention.

In the vibrator 20 according to this embodiment, buried members 48 as the anti-vibration members are embedded between the bridging portions 34a and 34b, and, the piezoelectric elements 30 and the electrode plates 32a and 32b. The buried member 48 has insulating properties and elastic properties. In this embodiment, the buried member 48 is formed of a silicone rubber. When the vibrator 20 vibrates ultrasonically, the buried members 48 interfere with vibration in any other direction except the longitudinal direction of the bridging portions 34a and 34b, and so occurrence of the vibration in any other direction except the longitudinal direction in the bridging portions 34a and 34b is suppressed.

Figure 5:
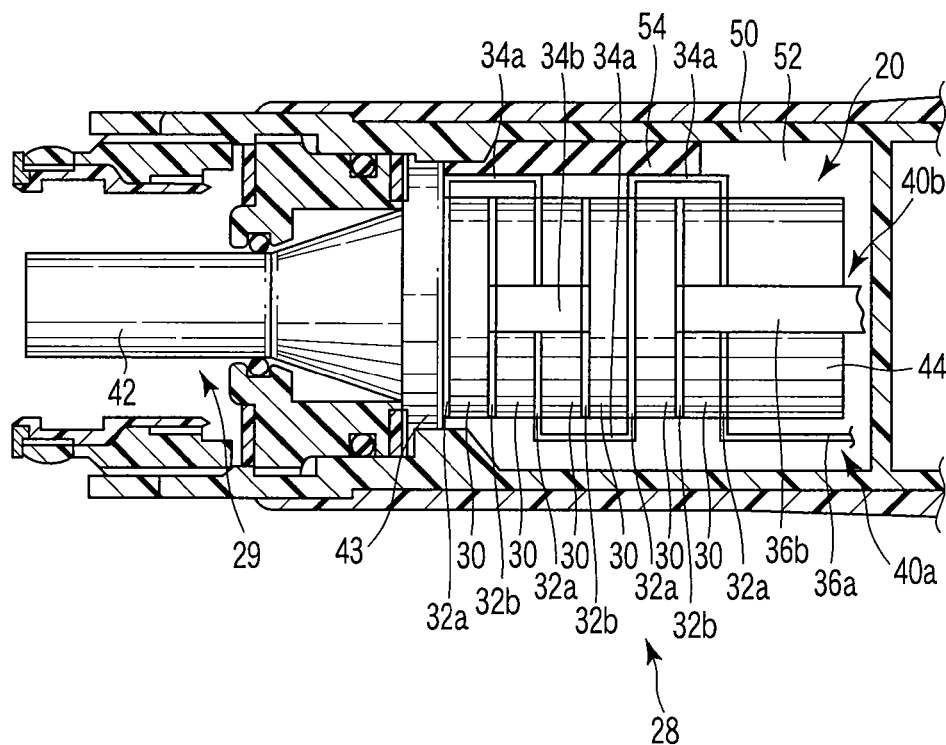
FIG. 5 is a partial cross-sectional side view showing a vibrator according to a third embodiment of the present invention.

FIG. 5 shows a third embodiment according to the present invention.

In the vibrator unit 18, the vibrator 20 is housed in a housing 50 as a housing portion, and the vibration generating portion 28 of the vibrator 20 is arranged in an airtight inner space 52. An interposed member 54 as the anti-vibration member is interposed between the housing 50 and the bridging portions 34a and 34b. The interposed member 54 has insulating properties and elastic properties, is compressed between the housing 50 and the bridging portions 34a and 34b, and gives the bridging portions 34a and 34b a radially inward load. In this embodiment, a rubber plate is used as the interposed member 54. When the vibrator 20 vibrates ultrasonically, the interposed member 54 gives the bridging portions 34a and 34b the radially inward load, and so the interposed member 54 prevents the bridging portions 34a and 34b from vibrating in any other direction except the longitudinal direction, and the interposed member 54 interferes with the vibration of the bridging portions 34a and 34b in any other direction except the longitudinal direction, and so occurrence of the vibration of the bridging portions 34a and 34b in any other direction other except the longitudinal direction is suppressed.

FIG. 6 shows a fourth embodiment according to the present invention.

In this embodiment, the inner space 52 where the vibration generating portion 28 is arranged is filled with a filling liquid 56 as an anti-vibration solution. The filling liquid 56 has insulating properties and relatively high viscosity. In this embodiment, a silicone oil is used as the filling liquid 56. When the vibrator 20 vibrates ultrasonically, the filling liquid 56 interferes with vibration of the bridging portions 34a and 34b in any other direction except the longitudinal direction, and so occurrence of the vibration in any other direction except the longitudinal direction in the bridging portions 34a and 34b is suppressed. Moreover, in a case where the inner space 52 is not filled with the filling liquid 56, when the ultrasonic accessory is subjected to, e.g., autoclave sterilization using high-temperature and pressure vapor, vapor may enter the inner space 52 of the housing 50, and droplets may adhere to a surface of the vibration generating portion 28, and so an electrostatic capacity of the vibration generating portion 28 may vary, and vibration characteristics of the vibrator 20 may change. In this embodiment, since the inner space 52 is filled with the insulative filling liquid 56, vapor is prevented from entering the inner space, and so a change in vibration characteristics of the vibrator 20 is prevented.

FIG. 7 shows a fifth embodiment according to the present invention.

In this embodiment, each of the electrode members 40a and 40b is formed of a soft flexible substrate. In this embodiment, the flexible substrate has a three-layer structure wherein a laminated layer 60 is sandwiched between a pair of conductive layers 58, the conductive layer 58 is formed of a copper foil, and the laminated layer 60 is formed of a polyimide film. In this manner, since each of the bridging portions 34a and 34b is formed of the soft flexible substrate, even if vibration occurs in the bridging portions 34a and 34b in any other direction except the longitudinal direction, the bridging portions 34a and 34b hardly fatigue, and so fracture of the bridging portions 34a and 34b is prevented.

Figure 8:
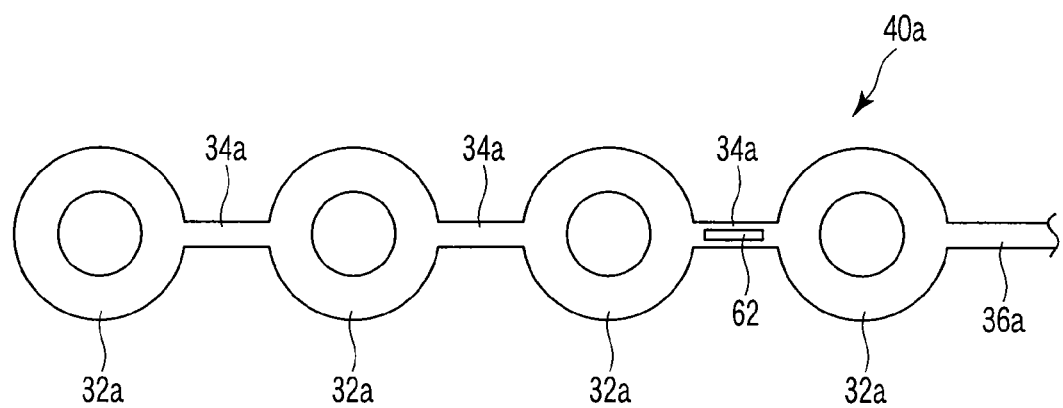
FIG. 8 is a development showing an electrode member according to a sixth embodiment of the present invention.

FIG. 8 shows a sixth embodiment of the present invention.

According to this embodiment, in at least one of electrode members 40 and 40b, e.g., the negative electrode member 40a, a slit 62 as a hole portion is formed in the bridging portion 34a closest to a voltage supply side, i.e., a proximal end side in the plurality of bridging portions 34a. Therefore, fatigue strength of this bridging portion 34a is smaller than fatigue strength of the bridging portion 34a on a voltage acceptance side, i.e., a distal end side with respect to the former bridging portion 34a. In a case where the respective bridging portions 34a have the same fatigue strength, when the vibrator 20 vibrates ultrasonically, the bridging portion 34a on the voltage acceptance side may fracture before the other bridging portions 34a. When the bridging portion 34a on the voltage acceptance side fractures, a change in electrostatic capacity of the vibrator 20 is small, matching of the system is maintained, and so the vibrator 20 may continue the vibration in an inappropriate vibration state. In this embodiment, since, in the plurality of bridging portions 34a and 34b, fatigue strength of the bridging portions 34a and 34b closest to the voltage supply side is smaller than fatigue strength of the bridging portions 34a and 34b on the voltage acceptance side with respect to the former bridging portion 34a, when the vibrator 20 vibrates ultrasonically, the former bridging portions 34a and 34b fracture first, the electrostatic capacity of the vibrator 20 is greatly changed, matching of the system is assuredly lost, and the system is securely stopped. Therefore, the vibrator 20 is prevented from continuing the vibration in the inappropriate vibration state.

It is to be noted that the slit 62 may be formed in lead portions 36a and 36b.

Figure 9:
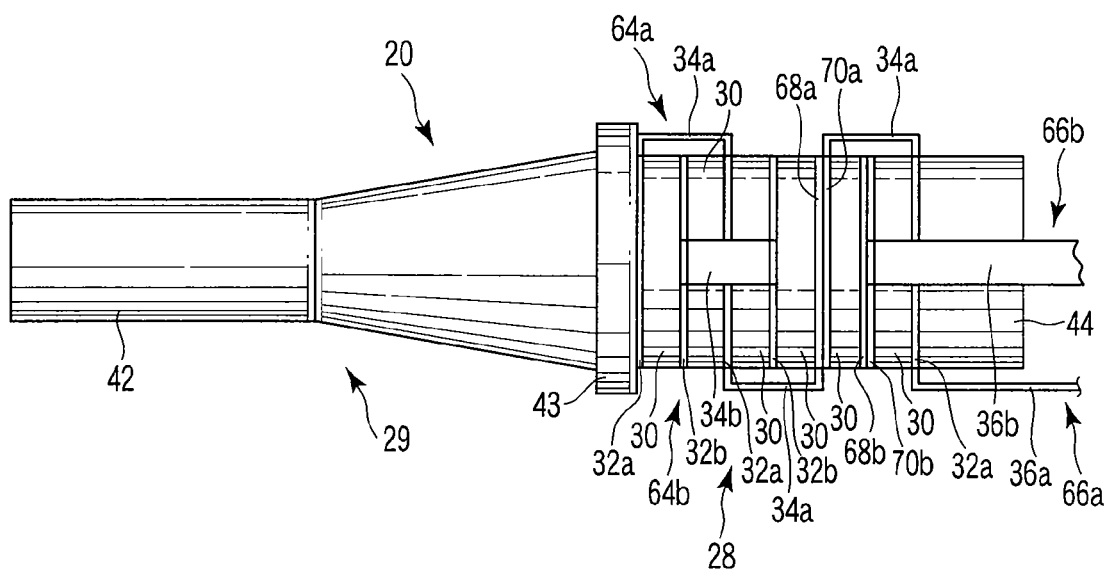
FIG. 9 is a side view showing a vibrator according to a seventh embodiment of the present invention.

FIG. 9 shows a seventh embodiment according to the present invention.

In this embodiment, distal-end-side electrode plates 64a and 64b on the voltage acceptance side and proximal-end-side electrode members 66a and 66b on the voltage supply side are used as the electrode members 40a and 40b. The electrode plates 68a and 68b at the most proximal ends of the distal-end-side electrode members 64a and 64b and the electrode plates 70a and 70b at the most distal ends of the proximal-end-side electrode members 66a and 66b are superimposed between the piezoelectric elements 30 adjacent to each other and are electrically connected with each other. Here, fatigue strength of a material forming the proximal-end-side electrode members 66a and 66b is smaller than fatigue strength of a material forming the distal-end-side electrode members 64a and 64b. In this embodiment, the proximal-end-side electrode members 66a and 66b are formed of, e.g., phosphor bronze or nickel silver, and the distal-end-side electrode members 64a and 64b are formed of, e.g., beryllium copper or a titanium copper. When the vibrator 20 vibrates ultrasonically, like the sixth embodiment, the bridging portions 34a and 34b of the proximal-end-side electrode members 66a and 66b on the voltage supply side fracture first, and so the vibrator 20 is prevented from continuing the vibration in an inappropriate state.

Figure 10:
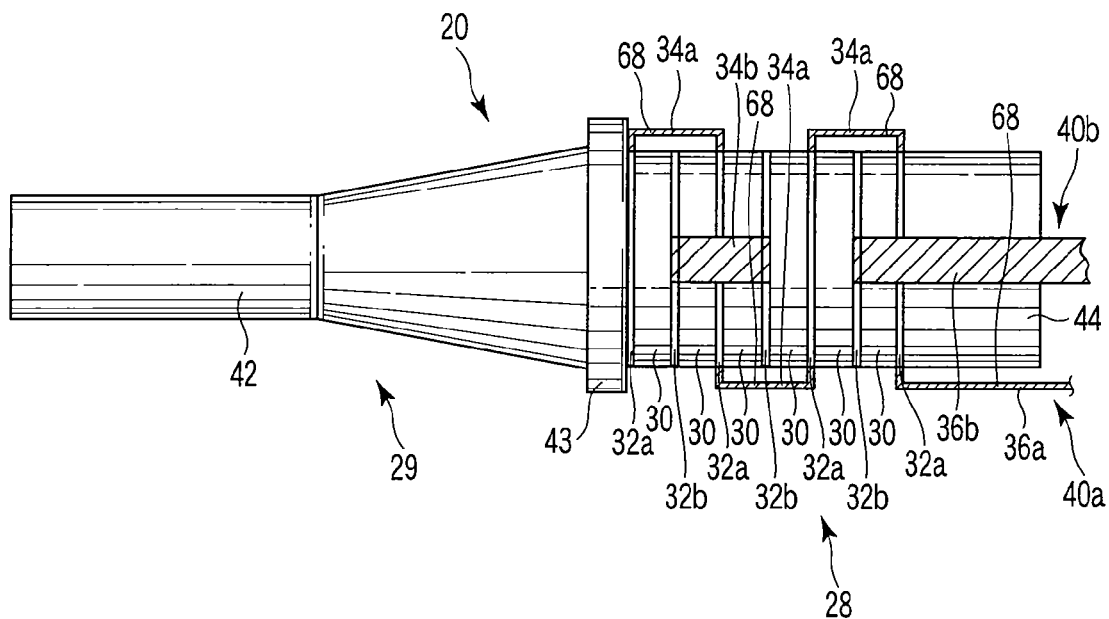
FIG. 10 is a side view showing a vibrator according to a reference embodiment according to the present invention.
Figure 11:
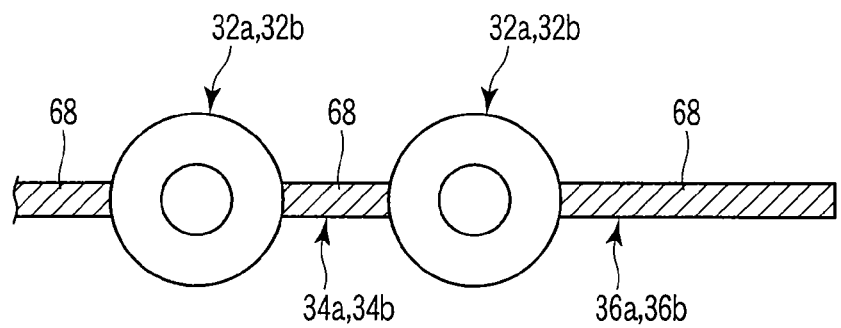
FIG. 11 is a development showing an electrode member according to the reference embodiment of the present invention.
Figure 12:
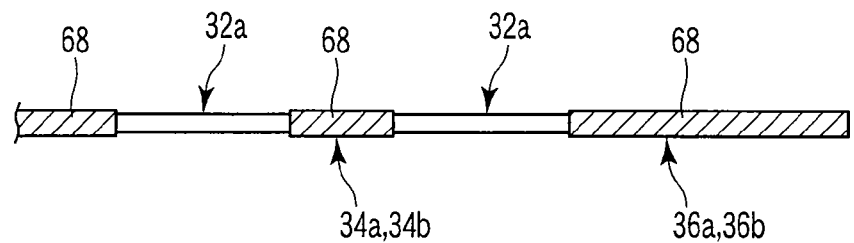
FIG. 12 is a side view showing the electrode member according to the reference embodiment of the present invention.

FIGS. 10 to 12 show a reference embodiment according to the present invention.

In an electrical insulating member of the reference embodiment, insulating wrappings 68 are provided on the bridging portions 34a and 34b and the lead portions 36a and 36b. In the vibration generating portion 28 of the vibrator 20, the bridging portions 34a and 34b and the lead portions 36a and 36b are arranged near the electrode plates 32a and 32b having the opposite polar. Therefore, in a case where the insulating wrappings 68 are not provided on the bridging portions 34a and 34b and the lead portions 36a and 36b, especially in a case where the vibrator 20 is small in size and the driving voltage is a high voltage in order to operate the vibrator 20 with a high output, short circuit may occur between the bridging portions 34a and 34b and the lead portions 36a and 36b, and, the electrode plates 32a and 32b having opposite pole. In this embodiment, since the insulating wrappings 68 are provided on the bridging portions 34a and 34b and the lead portions 36a and 36b, short circuit is prevented from occurring between the bridging portions 34a and 34b and the lead portions 36a and 36b, and, the electrode plates 32a and 32b having opposite pole, and so the vibrator 20 can be reduced in the size and increased in the output.

It is to be noted that insulating coating may be used in place of the insulating wrappings 68. In a case where the insulating coating is used, coating is applied to the bridging portions 34a and 34b and the lead portions 36a and 36b by, e.g., a spray or a brush in a state where the electrode plates 32a and 32b of electrode members 40a and 40b are protected, before assembling.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic vibration apparatus comprising a vibrator, wherein the vibrator includes:

at least two vibration elements to generate ultrasonic vibration when a driving voltage is applied to the vibration elements;

at least three electrode portions wherein the vibration elements and the electrode portions are alternately arranged side by side in a vibrating direction, the at least three electrode portions include a plurality of first electrode portions and at least one second electrode portion alternately arranged in the vibrating direction, the vibrator integrally vibrates ultrasonically in the vibrating direction when the driving voltage is applied to the first electrode portions and the second electrode portion;

a bridging portion coupling and electrically connecting two first electrode portions among the plurality of the first electrode portions to each other, the bridging portion having extended portions on both ends which extend from the two first electrode portions in a first direction and an intermediate coupling portion extending in a second direction and coupling both the extended portions;

a buried member as an anti-vibration member configured to be buried between the bridging portion, and each side surface of two adjacent vibration elements among the at least two vibration elements and a side surface of an electrode portion among the at least three electrode portions arranged between the two adjacent vibration elements and configured to suppress vibration of the bridging portion in any other direction except the vibrating direction.

2. The ultrasonic vibration apparatus according to claim 1, further comprising a housing portion housing the vibrator, wherein the anti-vibration portion includes an anti-vibration liquid filled into the housing portion.

3. The ultrasonic vibration apparatus according to claim 1, comprising:

at least the three first electrode portions; at least the two second electrode portions; and at least two bridging portions sequentially coupling at least the three first electrode portions, wherein fatigue strength of a bridging portion on a voltage supply side in at least the two bridging portions is smaller than fatigue strength of a bridging portion on a voltage acceptance side in at least the two bridging portions with respect to the bridging portion on the voltage supply side.

4. The ultrasonic vibration apparatus according to claim 3, wherein the bridging portion on the voltage supply side includes a hole portion.

5. The ultrasonic vibration apparatus according to claim 3, wherein fatigue strength of a material forming the bridging portion on the voltage supply side is smaller than fatigue strength of a material forming the bridging portion on the voltage acceptance side.

6. The ultrasonic vibration apparatus according to claim 1, wherein the first direction is radial and the second direction is longitudinal, relative to the ultrasonic vibration apparatus.

7. The ultrasonic vibration apparatus according to claim 1, wherein the buried member is formed of a silicone rubber.

* * * * *